US006801029B2

(12) United States Patent
van der Weide et al.

(10) Patent No.: US 6,801,029 B2
(45) Date of Patent: Oct. 5, 2004

(54) MICROWAVE DIELECTRIC SPECTROSCOPY METHOD AND APPARATUS

(75) Inventors: Daniel W. van der Weide, Madison, WI (US); Kimberly M. Taylor, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/269,833

(22) Filed: Oct. 11, 2002

(65) Prior Publication Data

US 2003/0090276 A1 May 15, 2003

Related U.S. Application Data

(60) Provisional application No. 60/328,961, filed on Oct. 12, 2001.

(51) Int. Cl.[7] ............................................. G01S 3/02
(52) U.S. Cl. ............................ 324/76.14; 324/76.19; 435/6
(58) Field of Search ............................ 324/637, 639, 324/640, 642, 644, 76.14, 76.15; 435/6

(56) References Cited

U.S. PATENT DOCUMENTS

| 5,334,941 | A | | 8/1994 | King ........................... 324/637 |
|---|---|---|---|---|
| 5,846,708 | A | | 12/1998 | Hollis et al. ..................... 435/6 |
| 5,858,666 | A | | 1/1999 | Weiss .............................. 435/6 |
| 6,287,776 | B1 | | 9/2001 | Hefti .............................. 435/6 |
| 6,287,874 | B1 | | 9/2001 | Hefti ........................... 436/501 |
| 6,338,968 | B1 | | 1/2002 | Hefti ........................... 436/518 |
| 6,340,568 | B2 | | 1/2002 | Hefti .............................. 435/6 |
| 6,368,795 | B1 | | 4/2002 | Hefti .............................. 435/6 |
| 6,376,258 | B2 | | 4/2002 | Hefti ........................... 436/518 |
| 6,395,480 | B1 | | 5/2002 | Hefti .............................. 435/6 |
| 6,449,580 | B1 | * | 9/2002 | Bardetsky et al. .......... 702/130 |
| 6,485,905 | B2 | | 11/2002 | Hefti .............................. 435/6 |
| 6,566,079 | B2 | | 5/2003 | Hefti ........................... 435/7.1 |
| 6,586,946 | B2 | * | 7/2003 | Hefti et al. ................. 324/636 |
| 6,617,861 | B1 | * | 9/2003 | Joshi ........................... 324/637 |
| 6,627,461 | B2 | | 9/2003 | Chapman et al. ........... 436/536 |
| 2002/0028461 | A1 | | 3/2002 | Hefti .............................. 435/6 |
| 2002/0072857 | A1 | | 6/2002 | Hefti ........................... 702/19 |
| 2002/0168659 | A1 | | 11/2002 | Hefti et al. ..................... 435/6 |
| 2002/0180570 | A1 | * | 12/2002 | Facer et al. ................. 333/239 |
| 2003/0032000 | A1 | | 2/2003 | Liu et al. ..................... 435/7.9 |
| 2003/0032067 | A1 | | 2/2003 | Hefti ........................... 435/7.9 |
| 2003/0072549 | A1 | | 4/2003 | Facer et al. ................. 521/146 |

FOREIGN PATENT DOCUMENTS

| EP | 0 519 250 | 12/1992 |
|---|---|---|
| WO | WO 00/28615 | 5/2000 |
| WO | WO 00/77501 | 12/2000 |
| WO | WO 01/20329 | 3/2001 |

OTHER PUBLICATIONS

Printout of Power Point presentation made by Daniel van der Weide at a bioscience symposium at Promega Corporation in Fitchburg, Wisconsin on May 25, 2001, entitled "Biosciences in the van der Weide Laboratory.".

(List continued on next page.)

*Primary Examiner*—N. Le
*Assistant Examiner*—Walter Benson
(74) *Attorney, Agent, or Firm*—Foley & Lardner LLP (57) ABSTRACT

Dielectric spectroscopy is carried out by coupling non-radiated microwave energy from an antenna to a sample to detect changes in the permittivity of the sample within the antenna's near field. The frequency response of the antenna exhibits resonant frequencies in a frequency range of interest. Changes in the sample as a result of changes in environmental conditions of the sample are exhibited as changes in the antenna's resonant frequency or frequencies. The changes in the positions of the peaks with changes in environmental conditions can be correlated to changes in the condition of the sample, such as unfolding of proteins with increases in temperature of the sample.

13 Claims, 6 Drawing Sheets

OTHER PUBLICATIONS

Geoff Smith, et al., "Dielectric Relaxation Spectroscopy and Sone Applications in the Pharmaceutical Sciences," Journal of Pharmaceutical Sciences, vol. 84, No. 9, Sep., 1995, pp. 1029–1044.

Camelia Gabriel, et al., "Dielectric Parameters Relevant to Microwave Dielectric Heating," Chemical Society Reviews, 1998, vol. 27, pp. 213–223.

Takashi Kamei, et al., "Hydration of Apomyoglobin in Native, Molten Globule, and Unfolded States by Using Microwave Dielectric Spectroscopy," Biophysical Journal, vol. 82, Jan., 2002, pp. 418–425.

Chonlarat Wichaidit, et al., "Resonant Slot Antennas as Transducers of DNA Hybridization: A Computational Feasibility Study," 2001 IEEE MTT–S International Microwave Symposium Digest, May 20, 2001, vol. 1, pp. 163–165.

G.R. Facer, et al., "Dielectric Spectroscopy for Bioanalysis: Form 40 Hz to 26.5 GHz in a Microfabricated Wave Guide," Applied Physics Letters, vol. 78, No. 7, Feb. 12, 2001, pp. 996–998.

Kimberly Taylor, et al., "Microwave Assay for Detecting Protein Conformation in Solution," Instrumentation for Air Pollution and Global Atmospheric Monitoring, Proceeds of SPIE, vol. 4574, 2002, pp. 137–143.

* cited by examiner

MICROWAVE DIELECTRIC SPECTROSCOPY METHOD AND APPARATUS

CROSS-REFERENCE TO RELATED APPLICATION

This application claims the benefit of provisional patent application No. 60/328,961, filed Oct. 12, 2001, the disclosure of which is incorporated herein by reference.

This invention was made with United States government support awarded by the following agency: NSF-0196021. The United States has certain rights in this invention.

FIELD OF THE INVENTION

This invention pertains generally to the field of microwave spectroscopy and particularly to dielectric spectroscopy apparatus and to assays of proteins and other biological molecules.

BACKGROUND OF THE INVENTION

Changes in the conformation of proteins in solution may occur for a variety of reasons, including ligand binding, enzyme activity, chemical or thermal denaturation and mutations or deletions. See, generally, T. E. Creighton, *Proteins: Structures and Molecular Properties*, $2^{nd}$ Ed. New York, W. H. Freeman & Company, 1993. Most researchers use optical methods to observe such changes, such as ultraviolet-visible (UV/VIS), fluorescence, or circular dichroism spectroscopies. Such optical methods generally require high protein concentrations and large volume, but optical spectroscopy instrumentation is readily available and analysis with such instrumentation is not difficult. Other, less common methods include differential scanning calorimetry and electron paramagnetic resonance. Protein structure may be explicitly determined using nuclear magnetic resonance or x-ray diffraction, but these direct methods are time consuming, complex and require specialized facilities or equipment.

An alternative method for detection of protein conformational changes employs dielectric dispersion of water at frequencies in the microwave range. All proteins have low permittivity due to the arrangement of charged residues, including the N- and C-temini, α-helices, and dipoles along the protein backbone. The static dielectric constant, $\epsilon'$, of a typical protein has been estimated as 2 to 5 at room temperature. R. Pethig, *Dielectric and Electronic Properties of Biological Materials*, Chichester, John Wiley & Sons, 1979. Pure water possesses a much larger dielectric constant, which is approximately 80 at 25° C. R. Pethig, ibid. All proteins are surrounded by one or more shells of "bound" water. Some proteins even have water molecules integrated into their structure. The presence of so much water hinders detection of the protein dielectric dispersion. However, this "bound" water may be distinguished from the water in bulk solution. In particular, the bound water undergoes dielectric dispersion at lower frequencies than water in bulk solutions. See, R. Pethig, "Protein Water Interactions Determined by Dielectric Methods," Annu. Rev. Phys. Chem., Vol. 43, 1992, pp. 177–205. Bound water will be released or rearranged in response to the changes in protein conformation, leading to changes in the permittivity of the solution. Measurements of such dielectric dispersion have conventionally been performed using time domain spectroscopy (TDS), waveguides, or coaxial probes. See, Y. Feldman, et al., "Time Domain Dielectric Spectroscopy: An Advanced Measuring System," Rev. Sci. Instrum., Vol. 67, 1996, pp. 3208–3216; G. R. Facer, et al., "Dielectric Spectroscopy for Bioanalysis: From 40 Hz to 26.5 GHz in a Microfabricated Wave Guide," Applied Physics Letters, Vol. 78, 2001, pp. 996–998; Y. Xu, et al., "On the Measurement of Microwave Permittivity of Biological Samples Using Needle-Type Coaxial Probes," IEEE Trans. Instrum. Meas., Vol. 42, 1993, pp. 822–827. TDS is by far the most common approach. TDS experiments involving protein conformational changes have been performed from 100 kHz to 10 GHz. Y. Feldman, et al., supra. TDS is not commonly used by biological scientists, possibly because of the complicated analysis that is required. Data must be converted from the time to the frequency domain, and then the response function must be transformed to complex permittivity.

SUMMARY OF THE INVENTION

In accordance with the present invention, dielectric spectroscopy is carried out by coupling microwave energy from the non-radiated field of an antenna to a sample solution to detect changes in permittivity of the sample within the antenna's non-radiated field. The antenna and its associated drive circuitry and components exhibit a resonant frequency or frequencies in a frequency range of interest, typically in the range from 0.5 GHz to 50 GHz. The frequency response of the antenna as coupled to the sample is determined. Changes in the sample as a result of changes in environmental conditions of the sample that change the permittivity of the same within the antenna's near zone will be manifested as changes in the magnitude or phase characteristics of the antenna's resonant frequency or frequencies. The frequency response of the antenna may be determined at selected times corresponding to changed environmental conditions of the sample, allowing changes in the frequency response of the antenna to be correlated with the changed environmental conditions. By carrying out dielectric spectroscopy in this manner, data collection and analysis is significantly simplified. Data is collected in the frequency domain, eliminating the need to convert data from the time domain to the frequency domain. Explicit determination of complex permittivity is not necessary. Analysis of data obtained in accordance with the invention is no more complicated than analysis of conventional optical spectroscopy data.

The apparatus of the present invention includes an antenna mounted with a sample container in position to have its non-radiated microwave near field coupled to a sample held within the container. A preferred antenna is a resonant slot antenna, for example, having a circular or rectangular slot configuration. The dimensions of the slot can be selected to obtain the desired frequency range for the system, and such resonant slot antennas can be obtained commercially or manufactured economically from available materials. The window in the antenna provided by the slot allows passage of a light beam, facilitating the combination of dielectric spectroscopy in accordance with the invention with conventional optical spectroscopy. In this manner, simultaneous measurements of dielectric dispersion and other phenomena can be performed. Such antennas may be miniaturized and integrated into semiconductor chips, allowing antennas to be placed into environments that are not suitable for conventional optical measurements. An antenna, as utilized in the invention, may be any element which allows coupling of the non-radiated microwave field to a sample, and is not limited to conventional antenna structures.

Further objects, features and advantages of the invention will be apparent from the following detailed description when taken in conjunction with the accompanying drawings.

DETAILED DESCRIPTION OF THE INVENTION

Figure 1:
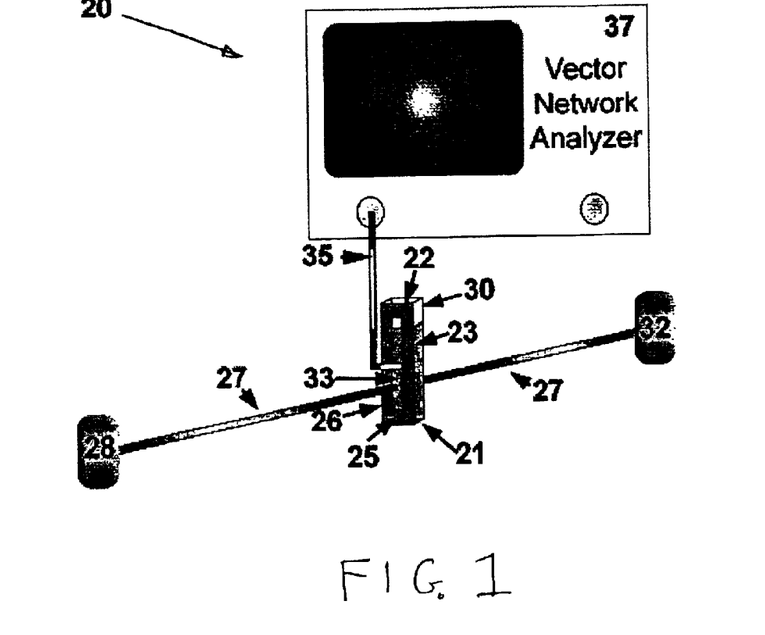
FIG. 1 is a schematic view of apparatus for carrying out microwave dielectric spectroscopy in accordance with the invention.
Figure 2:
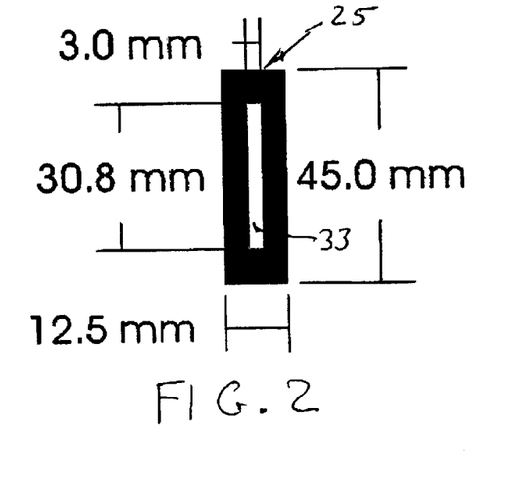
FIG. 2 is a plan view of a type of resonant slot antenna that may be utilized in the apparatus of FIG. 1, showing examples of dimensions that may be used for thermal unfolding experiments.

For purposes of illustrating the invention, microwave dielectric spectroscopy apparatus in accordance with the invention is shown generally at 20 in FIG. 1. The apparatus 20 includes a sample container or cuvette 21 with an interior cavity 22 which is suited to hold a liquid sample 23 therein for analysis. The form of the container 21 shown in FIG. 1 is for purposes of illustration only, and the container can have other geometric shapes including cylindrical, tubular, etc. A probe antenna 25 in accordance with the invention is mounted, for example, to the exterior surface of a sidewall 26 of the container 21. The sidewall 26 is preferably transparent to allow visual inspection of the contents of the container and to admit a light beam (shown schematically at 27) from the light source of a spectrometer 28. For optical transmission spectrometry, an opposite sidewall 30 of the container 21 is also preferably transparent so that the beam 27 can pass through the sample 23 and the sidewall 30 to a detector 32 of the spectrometer. The material forming the walls of the container 21 is preferably substantially transparent to microwave electromagnetic energy so that the non-radiated field from the antenna 25 can couple to sample material 23 within the cavity 22 of the container 21. The non-radiated field is generally within the near field of the antenna, typically within one wavelength from the antenna. C. A. Balanis, Antenna Theory: Analysis and Design, $2^{nd}$ Ed. New York: John Wiley & Sons, Inc., 1997. The antenna 25 may also be mounted to an inside surface of a wall of the sample container 21, to top or bottom walls as well as sidewalls, or suspended in the cavity 22 in contact with the sample 23 with the antenna preferably covered to be electrically insulated from the sample. A preferred form of the antenna 25 is a resonant slot antenna structure which has a central opening 33 that leaves an open area of the transparent sidewall 26 through which the light beam 27 can pass. FIG. 2 shows an example of such a resonant slot antenna structure (e.g., formed of thin conducting metal) with typical dimensions shown for use in thermal unfolding experiments. However, the antenna may have configurations other than a resonant slot structure. Combined dielectric and optical spectroscopy can also be performed by mounting the antenna at a position where it is out of the light beam, such as on the bottom surface of the container or on a sidewall which is not in the path of the light beam.

The antenna 25 is coupled via a connector 35, e.g., a coaxial cable, to a microwave frequency response analyzer 37 such as commercially available vector network analyzers, reflectometers or spectrum analyzers. The antenna 25 can also be coupled to another antenna (not shown) via free space coupling and thence to the analyzer, which facilitates array scanning. For example, an array of cuvettes with a slot antenna on the bottom of each cuvette may be analyzed sequentially by scanning a non-contact antenna (e.g., a coaxial cable with loop antenna) under the cuvettes to take readings from one cuvette at a time. The analyzer 37 provides microwave power on the cable 35 to the antenna 25 over a range of frequencies, and measures the response of the microwave system that is comprised of the cable 35, the antenna 25 coupled to the container 21, and the sample 23 held within the container. This microwave system, essentially comprising a two port device under test, will exhibit one or more resonant peaks centered at various frequencies. The center frequency or the magnitude (or both) of the peaks will be affected by the permittivity of the sample 23 because of interaction of the non-radiated electromagnetic field from the antenna and the sample. As this permittivity changes as a result of the effects of changes in environmental conditions within the container on the contents of the sample, characteristics of the resonances will change, such as shifts in the center frequencies or changes in the amplitudes of the resonant peaks. In accordance with the invention, the correlation of the changes such as the shift in the center frequencies or changes in amplitudes of the resonant peaks, can be correlated with changes in the environmental conditions applied to the sample to detect the effect of these changes in environmental conditions and to detect changes in characteristics of the sample itself.

The following are examples of microwave dielectric spectroscopy carried out in accordance with the invention.

Figure 4:
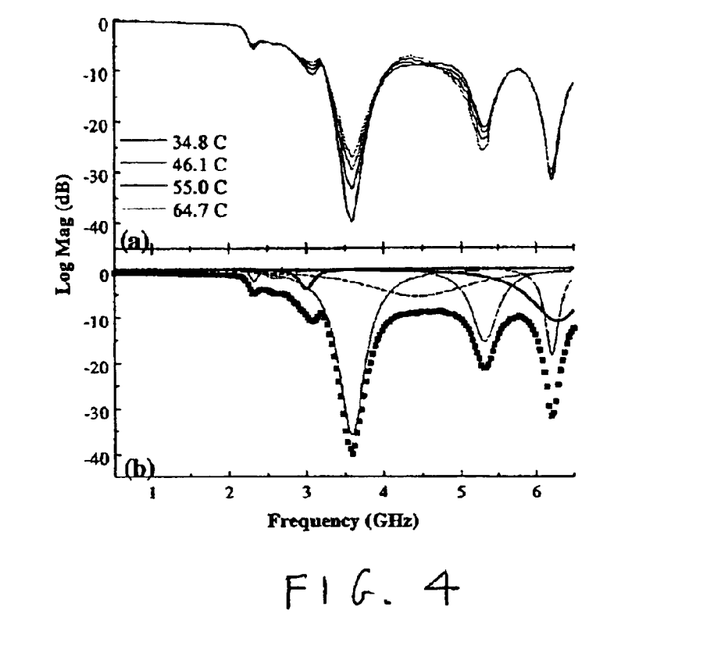
FIG. 4 are graphs in (a), above, showing the measured frequency response spectrum of buffer at selected temperatures and in (b), below, the fitting of the frequency response of the buffer at 34.8° C. to Lorentzian peaks.
Figure 6:
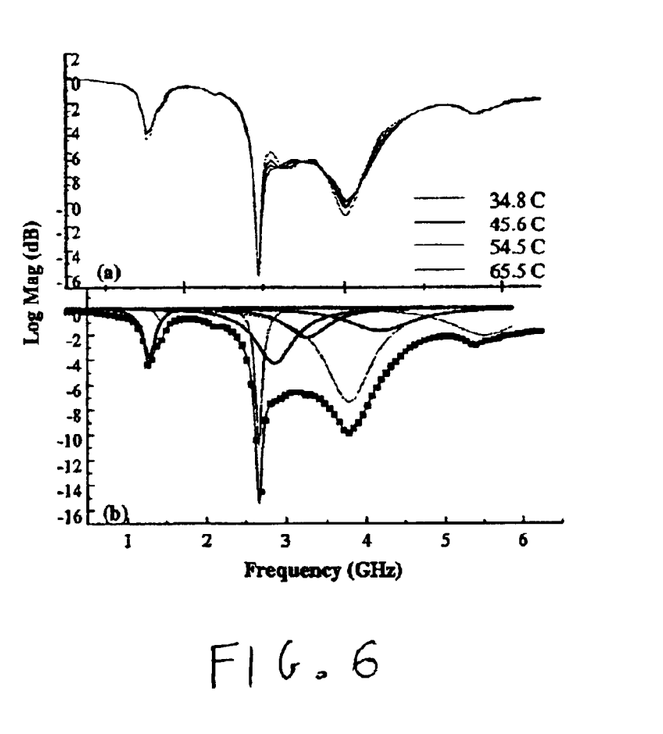
FIG. 6 are graphs in (a), above, illustrating the frequency response of RNase A at selected temperatures and in (b), below, the fitting of the frequency response at 34.8° C. to Lorentzian peaks (peaks 1, 4, 5 and 7 are indicated by solid lines).

A coaxial-fed slot antenna 25 was manufactured from RO-4002 (Rogers Corporation, Rogers, Conn.) on a LPKF ProtoMat using BoardMaster 3.0 (LPKF Laser & Electronics AG, Germany). The coaxial feed was composed of semi-rigid PE-047SR (Pasternack Enterprises, Irvine, Calif.). The dimensions of the antenna were chosen to yield a resonant frequency of approximately 3 GHz. This frequency was selected to optimize the interaction of microwave radiation with "bound water," assumed to undergo dispersion at lower frequencies than bulk solution. The active range of the antenna extends from approximately 500 MHz to 6.5 GHz. The antenna was attached to a 0.5 cm Suprasil fused quartz UV/VIS cuvette 21 (Hellma GmbH & Co., Germany). When attached to the cuvette, the antenna 25 exhibited not one but multiple resonant peaks, due to reflections from the cuvette 21 and higher order resonances in the antenna, as illustrated in FIGS. 4 and 6.

Microwave measurements were made utilizing as the analyzer 37 a Hewlett-Packard 8720D vector network analyzer (VNA) (Agilent Technologies, Palo Alto, Calif.) set to measure $s_{11}$. The lowest power range −15 to +5 dBm was used for all experiments. The slot antenna 25 was attached to the VNA 37 using a standard 50 Ω coaxial cable 35. UV/VIS absorption measurements were performed using a Hewlett-Packard 8452A diode-array spectrophotometer with a water-thermostatted cell holder (Agilent Technologies, Palo Alto, Calif.), functioning as the optical spectrometer 28 with detector 32. Both instruments were controlled using LabView (National Instruments Corporation, Austin, Tex.) via a GPIB connection.

Data analysis was performed in one of two ways: 1) Center frequency was determined by fitting spectra at each change of temperature or other environmental conditions to a number of Lorentzian peaks; or 2) Peak amplitude was determined for spectra at each change of temperature or other environmental condition. Commercial software such as Microcal Origin was used for both types of fitting. Data, either center frequency or amplitude, could be then plotted as a function of environmental condition and subjected to further analysis. For thermal unfolding experiments, peak center frequency determination yielded better results, perhaps because many peaks overlap. Peak amplitude determination was more successful for hormone binding experiments, probably because peaks were well-spaced and non-overlapping.

Bovine pancreatic ribonuclease A (RNase A) was purchased from Sigma (St. Louis, Mo.) and used without further purification. All other reagents were purchased from Fisher Scientific (Pittsburgh, Pa.). Lyophilized protein was dissolved in a solution of 30 mM sodium acetate/acetic acid, 100 mM sodium chloride, pH 4.5, then dialyzed exhaustively before use. Protein concentrations were determined by UV-VIS spectroscopy. The extinction coefficient was taken as 0.72 mg$^{-1}$mL cm$^{-1}$ at 278 nm. Concentrations of RNase A varied from 0.2 to 1 mg/mL (14.6 to 73.0 μM). The environmental condition of the sample that was changed was temperature. RNase A was unfolded reversibly by increasing the temperature of the sample at a maximum rate of 0.4° C./min. The unfolding reaction was monitored using UV/VIS absorbance at 288 nm.

The unfolding of RNase A may be observed using UV/VIS absorbance. At low protein concentrations, the absorbance of RNase A follows Beer's Law:

$$A(\lambda) = \epsilon(\lambda, T) \cdot c \cdot l$$

where A(λ) is the absorbance, ε(λ,T) is the extinction coefficient, c is the protein concentration, and l is the path length. For selected proteins, the extinction coefficient ε depends not only on the wavelength λ and the temperature T, but also on the protein conformation. Such a dependence of ε on conformation is called a hyperchromic shift. For RNase A, the maximal hyperchromic shift occurs at approximately 288 nm.

RNase A undergoes reversible two-state unfolding when the temperature of the protein solution is slowly increased:

$$N \xrightleftharpoons{K} U$$

$$\Delta H = \Delta H_m + \Delta C_P(T - T_m)$$

$$\Delta S = \Delta H_m / T_m + \Delta C_P \ln(T / T_m)$$

$$\Delta G = \Delta H - T\Delta S = -RT\ln K$$

$$F_N = \frac{1}{1+K} = 1 - F_U$$

$$\alpha = \alpha_N F_N + \alpha_U F_U$$

Figure 3:
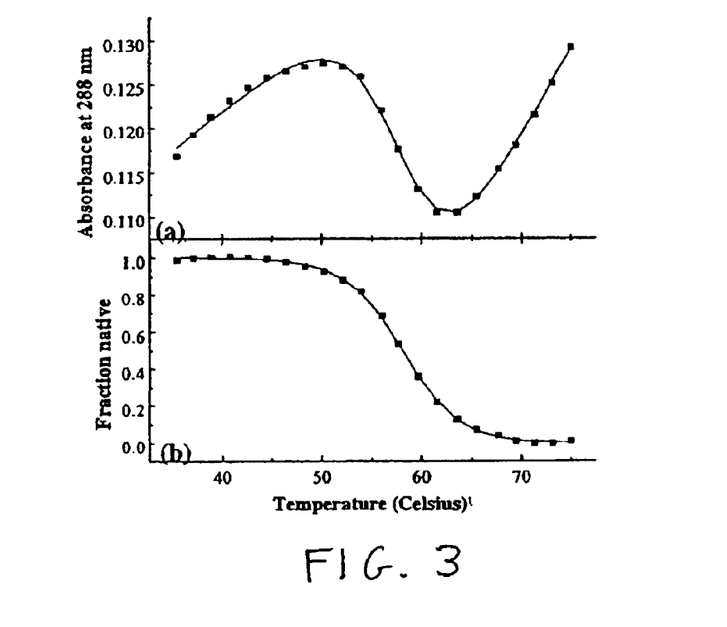
FIG. 3 are graphs in (a), above, illustrating the thermal melting of RNase A as monitored by UV/VIS absorbance at 288 nm and in (b), below, the fraction of RNase remaining in the native conformation as a function of temperature.

Here, N refers to native protein, U refers to unfolded protein, $T_m$ is the midpoint temperature (at which $F_N = F_U = 0.5$ and $\Delta G = 0$ kcal/mol), $\Delta H_m$ is the enthalpy at the midpoint temperature, α is the observed signal (in this case, UV/VIS absorbance), and $\alpha_N$ and $\alpha_U$ are the observed signals for native and unfolded protein, respectively. Since the unfolding of RNase A is a unimolecular reaction, thermodynamic parameters such as enthalpy, free energy, and mid-point temperature are independent of concentration. Such two-state unfolding exhibits a sigmoidal shape characteristics of a cooperative transition, as seen in FIG. 3(a). Analysis of unfolding of RNase A yields an average $T_m$ of 58.2° C. and an average $\Delta H_m$ of 74.9 kcal/mol. These values are comparable to previously published results.

The thermal response of the buffer alone (30 mM sodium acetate/acetic acid, 100 mM sodium chloride, pH 4.5) was investigated by slowly heating the solution under the same conditions used for protein unfolding. The frequency response of the buffer, measured as $s_{11}$ log mag, with temperature changes is shown in FIG. 4.

Figure 5:
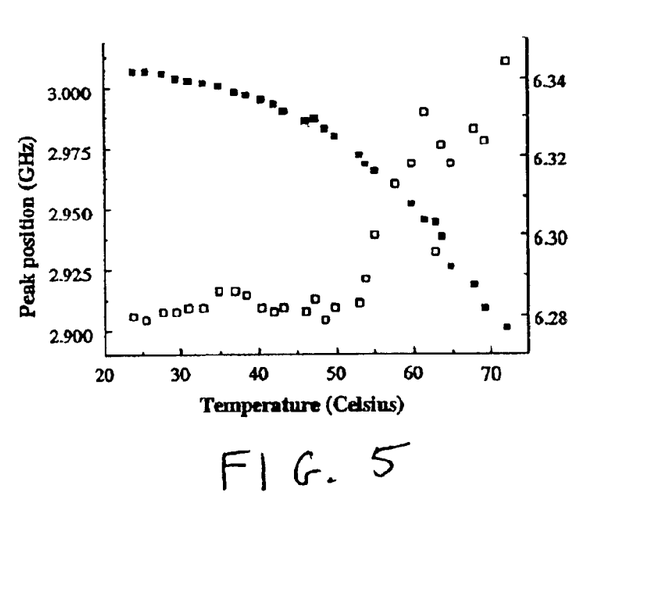
FIG. 5 are graphs illustrating the variations in peaks 3 (solid squares) and 8 (open squares) of FIG. 4 with changes in temperature.

Spectra were fit to Lorentzian peaks. Eight peaks were required to give a good fit ($R^2$ of 99.8% or better at all temperatures). All peaks became broader as the temperature was increased. Peak positions shifted monotonically with temperature. Some peaks, especially peak 8, at approximately 6.3 GHz at room temperature, increased in frequency with temperature. Most peaks, such as peak 3, at approximately 3.0 GHz at room temperature, decreased in response to temperature. Changes in center frequency of peaks 3 and 8 as a function of temperature are shown in FIG. 5.

As expected, the characteristic sigmoidal shape characteristic of cooperative unfolding was not seen for heating a buffer alone. Not all peaks yield a uniform temperature response. The frequency response of buffer alone probably reflects the response of water shells surrounding ions as well as bulk water. The permittivity of bulk water decreases with increasing temperature, as the extensive hydrogen bond networks are weakened or broken. Peaks corresponding to bulk water should then exhibit temperature-dependent increases in peak position, as evidenced by peak 8.

Thermal response of the spectra of RNase A, also measured as $s_{11}$ log mag, is shown in FIG. 6. As with buffer alone, peak positions shift with temperature, and most peaks broaden with increasing temperature.

Spectra were fitted to eight Lorentzian peaks. As with buffer alone, peaks did not respond uniformly to temperature. Four peaks, identified in Table 1 below, responded in a sigmoidal fashion characteristic of cooperative unfolding; the remaining peaks increased or decreased monotonically with temperature. The fits of the selected peaks to a 2-state unfolding model are shown in FIG. 6.

TABLE 1

Fits of selected Lorentzian peaks to 2-state unfolding model

| Peak number | Position at 30° C. (GHz) | Tm (° C.) | ΔHm(kcal/mol) |
|---|---|---|---|
| 1 | 1.5 | 50.4 | 66.0 |
| 4 | 3.1 | 58.3 | 161.4 |
| 5 | 3.5 | 53.3 | 72.1 |
| 7 | 4.4 | 60.9 | 76.8 |
| All peaks | | 55.21 | 54.2 |

Fitting to log mag peaks always results in a lower midpoint temperature ($T_m$) and unfolding enthalpy ($\Delta H_m$) than fitting to UV/VIS absorbance. This result is thought to be due to the difference in the phenomena being measured. UV/VIS absorbance measures environment-dependent changes in absorbance of aromatic amino acids (tryptophan, tyrosine, cystine). Electromagnetic measurements in the microwave range measure the dielectric dispersion of water, particularly bound water. It is not surprising that these two methods result in similar, but not identical, thermodynamic parameters. Such discrepancies are not unknown: protein unfolding as measured by UV/VIS spectroscopy and differential scanning calorimetry yield slightly different values of $T_m$ and $\Delta H_m$.

Figure 7:
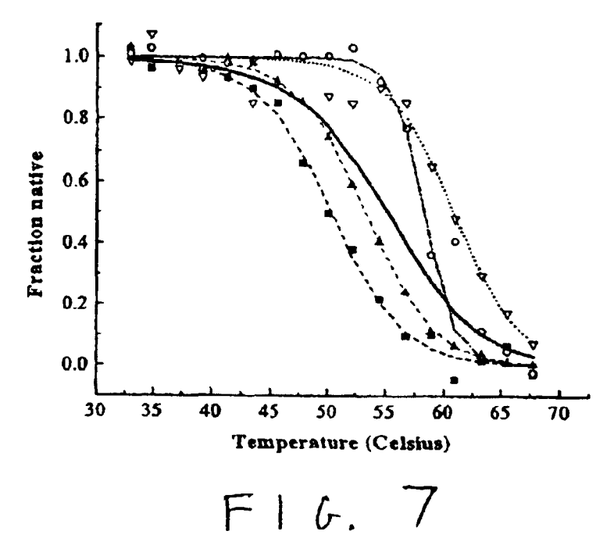
FIG. 7 are graphs showing fits of selected Lorentzian peaks to a two-state unfolding model, in which the heavy line is a fit to all peaks. Symbols: peak 1 (■), peak 4 (○), peak 5 (▲), peak 7 (▽).
Figure 8:
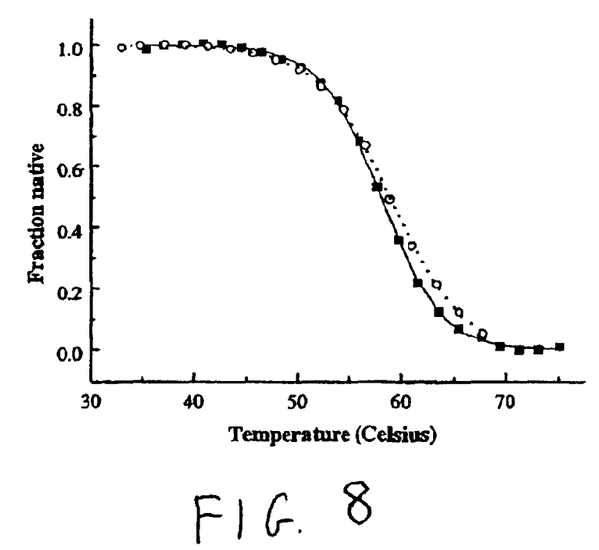
FIG. 8 are graphs showing the fraction of RNase A in the native conformation from UV/VIS absorbance alone (■) and simultaneous UV/VIS and microwave measurements (○) in accordance with the invention.

Other researchers have implied that the presence of microwave radiation destabilizes protein, and may enhance rates of folding and unfolding. Simultaneous UV/VIS absorbance measurements indicate that the presence of microwave radiation does not destabilize the protein at the power levels and protein concentrations used. FIG. 7 shows data from simultaneous UV/VIS absorbance and microwave measurements, and from UV/VIS absorbance alone and Table 2 summarizes the thermodynamic parameters. The differences in $T_m$ and $\Delta H_m$ are within experimental error and are not thought to be significant.

TABLE 2

Thermodynamic parameters from UV/VIS absorbance, and from simultaneous UV/VIS and microwave measurements

| Source | ΔH$_m$(kcal/mol) | T$_m$(° C.) |
|---|---|---|
| UV/VIS alone | 76.8 | 58.09 |
| Simultaneous UV/VIS and microwave | 65.1 | 58.91 |

The foregoing data indicate that the co-axial fed resonant slot antenna of the invention is suitable for measuring changes in the conformation of proteins in solution. Changes in permittivity within the antenna's near zone, thought to be due to release or reorganization or water shells surrounding the protein, are reflected as shifts in the antenna's resonant peaks. The spectra in the frequency domain may be fitted to multiple Lorentzian peaks. The thermal response of these peaks yields sigmoidal curves typical of cooperative unfolding. When fitted to a two-state model, these curves yielded values of midpoint temperature ($T_m$) and unfolding enthalpy ($\Delta H_m$) very similar to those reported by other researchers. Such a sigmoidal response was absent when a solution of buffer alone was heated under the same conditions.

Initial results indicate that the protein is not destabilized by the presence of microwave radiation. All experiments were performed at a low power range (−15 to +5 dBm). When unfolding of RNase A was monitored by UV/VIS absorbance in the presence or absence of microwave radiation, results were identical within experimental error.

Initial investigations on the effect of microwave power on protein unfolding indicate that, contrary to expectations, the protein is not affected by the presence of microwave radiation.

Figure 9:
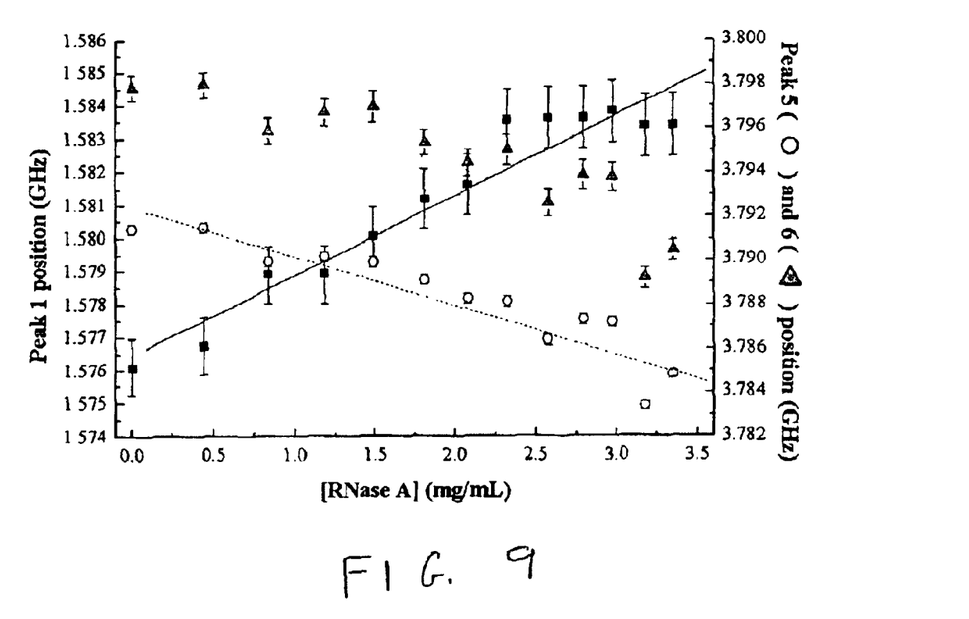
FIG. 9 are graphs illustrating the position of the frequency response peaks versus the concentration of RNase A.

Dielectric spectroscopy in accordance with the invention can be used to examine other sample characteristics in addition to the thermal unfolding of proteins. An example is detection of the presence of RNase A. When a buffer solution was titrated with concentrated RNase A, the position of selected peaks was found to vary approximately linearly with protein concentration. These peak shifts were very small, but far greater than the error in peak position (5 MHz or less). Such changes in protein concentration are reflected as changes in peak position, as illustrated in FIG. 9. Any water-soluble solute should have a similar effect, and future titrations with alcohols, salts, and other substances may be utilized.

As further examples, the invention may be used to detect the binding of small ligands to receptors. An antenna 25 as discussed above was inserted into the cell holder of a Beacon fluorescence polarization instrument from Panvera LLC, Madison, Wis. This slot antenna's resonant peaks are in the range of 10–20 GHz. By utilizing the invention in this manner, it is possible to simultaneously record fluorescence polarization (FP) and dielectric spectroscopy data.

A suitable example system is an estrogen receptor-β kit produced by Panvera, consisting of human recombinant estrogen receptor β (ERβ), fluormone ES2 (ES2), a fluorescently labeled estradiol, and appropriate buffer. The system is intended for use in a competition assay, in which a test compound T displaces ES2 from its binding site:

T+ERβ/ES2*↔ERβ/T+ES2

When bound to ERβ, ES2 tumbles slowly and has a high polarization (designated by an asterisk in the expression above). Unbound ES2 tumbles quickly and displays low polarization. The two compounds used to test this combined Beacon and dielectric spectroscopy system were estradiol and tamoxifen.

The following is the basic protocol used for the competitive binding assays:

300–500 μL (higher volume works best) of solution was used per test tube. The Beacon manual recommends only 100–200 μL, but this is not enough to completely cover the antenna configuration, and the results are unpredictable at this smaller volume.

The volume per test tube is made up by mixing 50% v/v of a fluormone/estrogen receptor 2× complex and 50% v/v of a serial dilution of the competitor:

(a) fluormone/estrogen receptor 2× complex: 2 nM fluormone, 20 nM estrogen receptor;

(b) competitor: initial concentration should be ~1 μM or higher to detect completely competitor/bound estrogen-receptor. Dilute competitor 2× serially to obtain range of competitor concentrations from 1 μM down to 0.01 nM or so (13–15 serial dilutions).

After mixing 50% 2× complex and 50% competitor, allow test tubes to incubate for 2 hours at room temperature in the dark.

When reading fluorescence polarization and VNA results, it is helpful to let each test tube sit for 4–5 minutes in the Beacon to bring the solution to an equilibrium temperature. VNA measurements were the difference in log mag between $s_{22}$ and $s_{11}$, where $s_{22}$ was the reflected signal from the sample and $s_{11}$ was the signal from a coaxial cable of the same length as that used to drive the antenna. The purpose of this subtraction was to minimize instrument noise and drift.

The basic protocol for the kinetic binding assay is the same as the competitive binding assay. Typically, one starts with a competitor concentration of 100 nM, and serially dilute to obtain 3 different concentrations (we dilute to various concentrations, from 2× to 100× depending on the circumstances). After combining the 2× complex with the competitor, quickly mix the two thoroughly and start monitoring using the Beacon and VNA. Note: due to inadequate thermal equilibrium, the initial VNA reading is usually not usable.

A third assay is a general binding assay, used to find the Kd of single ligand, e.g., Panvera fluormone. Enough fluormone stock at 0.5–1 nM is prepared for 13–15 test tubes (~3–3.5 mL). A small volume of concentrated estrogen receptor is then made up (~200 nM, or as high as we can get), and diluted serially into separate tubes to get a range of concentrations down to ~0.01 nM. The fluormone stock and estrogen receptor dilutions are then combined in equal volumes. Technically, the reaction is instantaneous and incubation is not needed. An alternative to serial dilution of estrogen receptor is to start with a single tube of concentrated estrogen receptor, then dilute that tube 10–15× with the fluormone stock, taking a reading on the Beacon and VNA at each stage.

Figure 10:
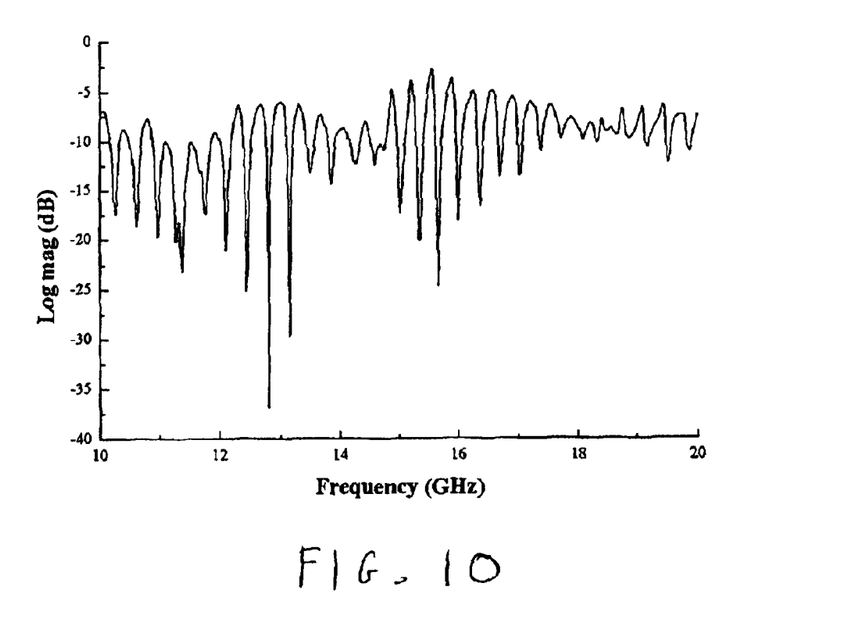
FIG. 10 is a graph showing the frequency response spectrum of 0.24 nM fluormone ES2, 180 nM estrogen receptor β at 25° C.
Figure 11:
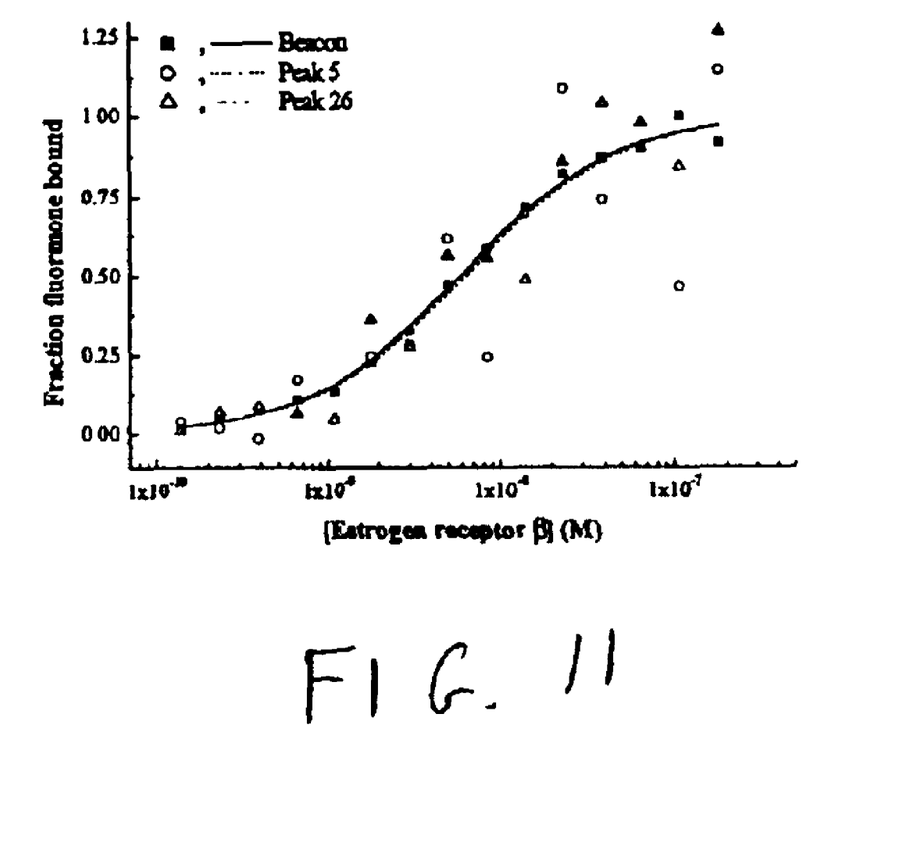
FIG. 11 is a graph illustrating the binding of fluormone ES2 to estrogen receptor β.

In initial experiments, data from the Beacon for competition of estradiol or tamoxifen with ES2 was nearly identical to published data and highly reproducible. The microwave response spectrum from 10–20 GHz, measured as described above by the VNA 37, consists of approximately 30 sharp peaks as shown in FIG. 10. Although peak position does not change appreciably, peal magnitude was amenable to analysis, allowing data to be obtained for competition kinetics. The relationship between peak position and time was exponential as expected, and similar to results from the Beacon. It was found that the antenna was extremely sensitive to the volume of solution. The literature from Panvera recommends that only 100–200 μL of solution are necessary. However, a volume of at least 400 μL is needed to completely cover the antenna when it is configured on the side of cuvette (rather than on the bottom of the cuvette). The $K_d$ of ES2 binding to ERβ was determined. When the appropriate volume of solution was used, binding curves could be obtained using peak amplitudes from the antenna, as shown in FIG. 11, and binding data is given in Table 3 below.

TABLE 3

$K_d$ for binding of fluormone ES2 to estrogen receptor β (25° C.)

| Source/Peak # | $K_d$(nM) |
| --- | --- |
| Beacon | 5.843 ± 0.480 |
| Peak 5 (11.75 GHz) | 6.311 ± 4.447 |
| Peak 26 (18.663 GHz) | 6.034 ± 3.450 |

The $K_d$ value obtained from the Beacon is much higher than the published value of ~2 nM. The reason for this difference is not known. Peaks 5 and 26 yielded a $K_d$ similar to that of the Beacon; other peaks yield $K_d$ values that vary between 1.939±1.121 and 8.779±6.267 nM. Different peaks may yield different $K_d$'s due to uncertainty in the values of peak position when 100% and 0% bound. It is noted that the system is sensitive not only to volume but also to temperature. It is necessary to let a solution incubate in the Beacon's cell holder at least 5 minutes before recording a spectrum to achieve thermal equilibration. Even small changes (from 22° C. to 20° C., for example) can cause large changes in peak magnitude. For this reason, the first five minutes of any competition kinetics are usually unusable.

The present invention may be utilized for drug discovery and other binding studies. In most conventional binding studies, the receptor and/or ligand must be labeled in order to detect binding. Fluorescent or UV-active labels tend to be large and may affect the binding. Fluorescence polarization requires that ligands be extremely small compared to the receptor, so that the system cannot be used for many receptor/ligand combinations. Radiolabeling does not interfere with binding, but experiments tend to be slow and disposal of the labeled reagent can be problematic. The present invention, which requires no labeling of receptor or ligand, is not subject to these problems. In theory, the receptor and ligand can be of any size, as long as the bound water shells are sufficiently perturbed by the binding.

It is understood that the invention is not limited to the embodiments set forth herein as illustrative, but embraces all such forms thereof as come within the scope of the following claims.

What is claimed is:

1. Microwave dielectric spectroscopy apparatus comprising:
    (a) a container having a cavity for holding a sample to be analyzed;
    (b) a microwave antenna mounted with the container in position to couple non-radiated microwave field from the antenna to a sample held in the cavity of the container;
    (c) a microwave frequency response analyzer coupled to the probe antenna to provide microwave power thereto and to determine the frequency response of the antenna and the effect of the sample on the frequency response of the antenna; and
    (d) wherein the container is formed of a material that is transparent to microwave radiation and wherein the antenna is mounted on an exterior surface of the container with the near field of the antenna coupled to a sample held within the container through the wall of the container.

2. The apparatus of claim 1 wherein the antenna comprises a resonant slot antenna.

3. The apparatus of claim 1 wherein the analyzer is a vector network analyzer.

4. The apparatus of claim 1 wherein the analyzer is a reflectometer.

5. The apparatus of claim 1 wherein the antenna is a resonant slot antenna mounted on an outer surface of the container.

6. The apparatus of claim 1 wherein the analyzer provides microwave power to the antenna over a range of frequencies from 0.5 GHz to 50 GHz.

7. The apparatus of claim 1 wherein the container has an optically transparent wall and further including an optical spectrometer mounted to provide a light beam to the sample through the transparent wall of the container to carry out optical spectroscopy on the sample.

8. Microwave dielectric spectroscopy apparatus comprising:
    (a) a container having a cavity for holding a sample to be analyzed;
    (b) a microwave antenna mounted with the container in position to couple non-radiated microwave field from the antenna to a sample held in the cavity of the container;
    (c) a microwave frequency response analyzer coupled to the antenna to provide microwave power thereto and to determine the frequency response of the antenna and the effect of the sample on the frequency response of the antenna; and
    wherein the container has optically transparent sidewalls, and further including an optical spectrometer mounted to provide a light beam to the sample through a transparent sidewall of the container to carry out optical spectroscopy on the sample.

9. The apparatus of claim 8 wherein the antenna comprises a resonant slot antenna and wherein the slot of the resonant slot antenna is positioned over a transparent sidewall of the container to allow the light beam of the optical spectrometer to pass therethrough.

10. Microwave dielectric spectroscopy apparatus comprising:
    (a) a container having a cavity for holding a sample to be analyzed;
    (b) a microwave antenna mounted with the container in position to couple non-radiated microwave field from the antenna to a sample held in the cavity of the container; and
    (c) a microwave frequency response analyzer coupled to the probe antenna to provide microwave power thereto and to determine the frequency response of the antenna and the effect of the sample on the frequency response of the antenna; and
    wherein the antenna is a resonant antenna having a primary resonant frequency of approximately 3 GHz.

11. A method of carrying out dielectric spectroscopy comprising:
    (a) providing a sample to be analyzed held in a container;
    (b) coupling non-radiated microwave field from an antenna to the sample held in the container and applying microwave power to the antenna over a range of frequencies and determining the frequency response of the antenna over a selected frequency range;
    (c) changing the environmental conditions of the sample within the container in a series of changed conditions and determining the microwave frequency response of the antenna at the series of changed conditions; and
    (d further including determining the resonant peaks in the frequency responses at each of the environmental conditions and determining changes in the center frequency or amplitude or both of the resonant peaks as a function of the environmental conditions.

12. The method of claim 11 wherein the sample includes proteins that undergo reversible unfolding as a function of temperature and in changing the environmental conditions, the temperature of the sample is changed.

13. The method of claim 12 further including determining peaks in the frequency response of the antenna that change in center frequency or amplitude or both as a function of the temperature of the sample.

* * * * *